United States Patent
Wczasek et al.

(10) Patent No.: US 8,157,909 B2
(45) Date of Patent: Apr. 17, 2012

(54) MIXTURE OF COPPER-CONTAINING METAL EFFECT PIGMENTS AND METHOD FOR THE PRODUCTION THEREOF

(75) Inventors: Katrin Wczasek, Nürnberg (DE); Michael Becker, Lauf (DE); Svea Heitmar, Neuhaus/Pegnitz (DE); Dieter Proelss, Schwabach (DE)

(73) Assignee: Eckart GmbH (DE)

( * ) Notice: Subject to any disclaimer, the term of this patent is extended or adjusted under 35 U.S.C. 154(b) by 0 days.

(21) Appl. No.: 12/993,128

(22) PCT Filed: May 28, 2009

(86) PCT No.: PCT/EP2009/003795
§ 371 (c)(1), (2), (4) Date: Feb. 25, 2011

(87) PCT Pub. No.: WO2009/149834
PCT Pub. Date: Dec. 17, 2009

(65) Prior Publication Data
US 2011/0139034 A1 Jun. 16, 2011

(30) Foreign Application Priority Data

May 28, 2008 (EP) ................................. 08009699
Mar. 5, 2009 (EP) ................................. 09003175

(51) Int. Cl.
C09C 1/62 (2006.01)
C09C 1/66 (2006.01)
C09D 5/36 (2006.01)
C09D 7/12 (2006.01)

(52) U.S. Cl. ........................ 106/480; 428/402
(58) Field of Classification Search .............. 106/480; 428/402
See application file for complete search history.

(56) References Cited

U.S. PATENT DOCUMENTS

| | | | |
|---|---|---|---|
| 2,864,719 A | 12/1958 | Willis | |
| 4,884,754 A | 12/1989 | Kemp, Jr. et al. | |
| 6,398,861 B1 | 6/2002 | Knox | |
| 7,151,153 B2 | 12/2006 | Bruchmann et al. | |
| 7,485,365 B2 | 2/2009 | Schuster et al. | |
| 7,511,085 B2 | 3/2009 | Bruchmann et al. | |
| 2002/0050186 A1 | 5/2002 | Hanawa et al. | |
| 2004/0194663 A1 | 10/2004 | Li et al. | |
| 2006/0053968 A1* | 3/2006 | Schuster et al. | ............... 75/255 |
| 2006/0118663 A1 | 6/2006 | Herzing | |
| 2007/0199478 A1 | 8/2007 | Schlegl et al. | |
| 2010/0047199 A1 | 2/2010 | Trummer et al. | |
| 2010/0163420 A1 | 7/2010 | Weiss et al. | |

FOREIGN PATENT DOCUMENTS

| | | |
|---|---|---|
| DE | 10315775 A1 | 10/2004 |
| DE | 102006051893 A1 | 5/2008 |
| EP | 1553144 A | 7/2005 |
| EP | 1529084 B1 | 6/2006 |
| EP | 2128203 | 12/2009 |
| GB | 994409 A | 6/1965 |
| GB | 1264584 A | 2/1972 |
| WO | WO 02/36695 | 5/2002 |
| WO | WO 02/36697 | 5/2002 |
| WO | WO 2004/026972 A | 4/2004 |
| WO | WO 2006/066825 A | 6/2006 |
| WO | WO 2008/077612 A | 7/2008 |
| WO | WO 2009/144005 | 12/2009 |

OTHER PUBLICATIONS

International Search Report dated Mar. 25, 2010, issued in corresponding international application No. PCT/EP2009/003795.
European Search Report dated Oct. 31, 2008, issued in corresponding priority European application No. EP 08009699.3.
European Search Report dated Mar. 25, 2010, issued in corresponding priority European application No. EP 09003175.8.
European Examination Report dated Mar. 2, 2010, issued in corresponding priority European application No. EP 08009699.3.

* cited by examiner

Primary Examiner — Anthony J Green
(74) Attorney, Agent, or Firm — Ostrolenk Faber LLP

(57) ABSTRACT

A mixture of platelet-shaped, copper-containing metallic effect pigments having a copper content of 60% to 100% by weight, based on the total metal content, with at least one further component, where the copper-containing metallic effect pigments have a thickness distribution, determined via thickness counting by scanning electron microscopy (SEM) and represented as cumulative undersize distribution,
a) with an $h_{50}$ of 10 to 100 nm, and
b) with an $h_{90}$ of 20 to 150 nm, and in that the at least one further component is a cellulose derivative selected from the group consisting of alkylcellulose, hydroxyalkylcellulose, alkyl(hydroxyalkyl)cellulose, and mixtures thereof, and/or is at least one additive having antioxidative and/or radical-inhibiting properties. The disclosure further relates to a method for producing this mixture, and to a coating composition.

21 Claims, No Drawings

MIXTURE OF COPPER-CONTAINING METAL EFFECT PIGMENTS AND METHOD FOR THE PRODUCTION THEREOF

CROSS REFERENCE TO RELATED APPLICATIONS

The present application is a 35 U.S.C. §371 National Phase conversion of PCT/EP2009/003795, filed May 28, 2009, which claims benefit of European Application Nos. 08009699.3, filed May 28, 2008, and 09003175.8, filed Mar. 5, 2009, the disclosures of which are incorporated herein by reference. The PCT International Application was published in the German language.

TECHNICAL FIELD

The present invention relates to a mixture of copper-containing metallic effect pigments with at least one further component, to a coating composition comprising said mixture, and to an article comprising said mixture or said coating composition. The invention further relates to a method for producing a mixture of copper-containing metallic effect pigments with at least one further component.

BACKGROUND

Copper-containing metallic effect pigments, comprising copper pigments or brass pigments produced from a copper-zinc alloy, also referred to as gold bronze pigments, are used in industries including the graphics industry, as for example in printing inks.

The metallic effect pigments used to date for pigmenting flexographic and gravure inks and produced by milling from copper or brass powder, such as "Rotovario" gold bronze pigment dispersions or "Rotoflex" stabilized leafing gold bronze pigment powder or "Rotosafe" stabilized leafing gold bronze pigment pellets from Eckart GmbH, D-90763 Fürth, Germany, for example, are of only limited suitability for the pigmentation of film reverse applications with mirrorlike effect, on account of their leafing properties. The aforementioned copper-containing metallic effect pigments are obtained by dry milling of copper or brass powder.

The use in printing inks of brass pigments produced by PVD methods is also problematic in as much as homogeneous metallization of the two metals (copper and zinc) with very different vaporization temperatures in a high vacuum is extremely difficult from a technical standpoint, with the aim of achieving a uniform hue. Moreover, unlike the brass pigments produced by conventional milling, the PVD brass pigments, which are relatively expensive to produce, have layers which are not very compact, with densities below the densities of the respective materials, and the desired gold hues (especially rich gold) cannot be realized at the low layer thicknesses desired.

EP 1 529 084 B1 describes gold bronze pigments which can be produced by PVD methods. On account of the complex method, these pigments are very expensive. Moreover, these pigments tend toward partial phase separation of the alloying constituents, which is likewise accompanied by unwanted shifts in hue and by inadequate stabilities of hue.

GB 994,409 discloses a varnish, ink and paint composition which comprises copper-containing pigments and benzotriazole as corrosion inhibitor. The benzotriazole prevents discoloration of the varnish, paint or ink composition caused by oxidation of copper.

According to the teaching of EP 08009699.3, unpublished at the priority date of the present specification, copper-containing, platelet-shaped metallic effect pigments having improved optical properties are obtained when these pigments have a thickness distribution, determined by scanning electron microscopy (SEM) and represented as cumulative undersize distribution, with an $h_{50}$ of 10 to 50 nm and an $h_{90}$ of 20 to 70 nm.

It has now emerged that the copper-containing metallic effect pigments produced in accordance with the teaching of EP 08009699.3, on contact with binders of a coating composition, such as varnish, paint, printing ink, etc., may result in an unwanted increase in the viscosity of the varnish, paint or printing ink. This increase in viscosity of a coating composition, as of a printing ink, for example, which may also be referred to as gelling of the coating composition, as of the printing ink, for example, may take place within a few hours or days. A coating composition, as for example printing ink, which has undergone such gelling or is of high viscosity can no longer be applied—printed, for example—at all, or only with loss of the high-grade optical properties. If its viscosity is very high, the coating composition, as for example printing ink, can no longer be dispersed with addition of solvent, or else a very large quantity of solvent must be added, resulting in an impairment in quality in relation to the optical properties of the coating composition. In the case of a printing ink, for example, an increased quantity of solvent may lead to a significant detraction in the context of ink transfer during printing.

There is therefore a need for platelet-shaped, copper-containing metallic effect pigments which have outstanding optical properties, especially in the context of film reverse applications, and which do not give rise to an unwanted increase in viscosity following introduction into a coating composition.

SUMMARY

The object on which the invention is based is achieved through provision of a mixture of platelet-shaped, copper-containing metallic effect pigments having a copper content of 60% to 100% by weight, based on the total metal content, with at least one further component, where the copper-containing metallic effect pigments have a thickness distribution, determined via thickness counting by scanning electron microscopy (SEM) and represented as cumulative undersize distribution,
a) with an $h_{50}$ of 10 to 100 nm,
b) with an $h_{90}$ of 20 to 150 nm,
and in that the at least one further component is a cellulose derivative selected from the group consisting of alkylcellulose, hydroxyalkylcellulose, alkyl(hydroxyalkyl)cellulose, and mixtures thereof, and/or is at least one additive having antioxidative and/or radical-inhibiting properties. The $h_{98}$ here is preferably in a range of 21 to 200 nm, more preferably from 21 to below 80 nm.

Preferred developments of the invention are specified herein.

Furthermore, the object on which the invention is based is also achieved through provision of a coating composition, where the coating composition comprises a mixture as described herein and is preferably a printing ink, a printing ink concentrate, a varnish, a varnish concentrate, a paint or a paint concentrate.

Moreover, the object on which the invention is based is achieved through provision of a coated article, where the coated article comprises a mixture of copper-containing metallic effect pigments with at least one component as described herein or a coating composition as also described herein.

According to one preferred development, the article is transparent. The article is preferably a transparent film.

The object on which the invention is based is also achieved through provision of a method for producing a mixture of copper-containing metallic effect pigments with at least one component as described herein, where the method comprises the following steps:

(a) milling a copper-containing metal powder having a particle size distribution with a $d_{powder,50}$ of 1 to 180 µm and a $d_{powder,90}$ of 2 to 430 µm and having a copper content of 60% to 100% by weight, based on the total metal powder, to form platelet-shaped metallic effect pigments, using a milling mechanism, in the presence of lubricants and grinding media and optionally solvent, the resulting platelet-shaped metallic effect pigments having an average thickness, as determined via thickness counting by scanning electron microscopy (SEM), with an $h_{50}$ of 10 to 100 nm, preferably of 10 to 50 nm, and an $h_{90}$ of 20 to 150 nm, preferably of 20 to 70 nm, and (b) contacting the platelet-shaped, copper-containing metallic effect pigments obtained in step (a) with at least one component which is a cellulose derivative selected from the group consisting of alkylcellulose, hydroxyalkylcellulose, alkyl-(hydroxyalkyl) cellulose, and mixtures thereof, and/or is at least one additive having antioxidative and/or radical-inhibiting properties.

The object on which the invention is based is further achieved through the use of a mixture of platelet-shaped, copper-containing metallic effect pigments as described herein in a coating composition which is preferably in compacted form.

The object on which the invention is based is further achieved through the use of a cellulose derivative selected from the group consisting of alkylcellulose, hydroxyalkylcellulose alkyl(hydroxyalkyl)cellulose, and mixtures thereof for stabilizing platelet-shaped, copper-containing metallic effect pigments, such as brass effect pigments.

The object on which the invention is based is further achieved through the use of a cellulose derivative selected from the group consisting of alkylcellulose, hydroxyalkylcellulose, alkyl(hydroxyalkyl)cellulose, and mixtures thereof for stabilizing coating compositions which comprise platelet-shaped, copper-containing metallic effect pigments, such as brass effect pigments.

DETAILED DESCRIPTION

By stabilization is meant that the platelet-shaped, copper-containing metallic effect pigments are protected with respect to oxidation or that the platelet-shaped copper-containing metallic effect pigment-containing coating compositions are protected in relation to gelling and/or to an unwanted increase in viscosity.

The term "cumulative undersize distribution" used in accordance with the invention is also referred to as "cumulative frequency distribution". These two terms can therefore be used interchangeably, and hence in the present application the term "cumulative frequency distribution" may also be used in place of the term "cumulative undersize distribution".

The term "platelet-shaped, copper-containing metallic effect pigment" and the term "copper-containing metallic effect pigment" are presently used interchangeably.

The inventors have found that the unwanted increase in viscosity following incorporation of the platelet-shaped, copper-containing metallic effect pigments used in accordance with the invention into a binder-containing system, such as a coating composition, can be attributed to binder gelling.

The inventors suppose, without wishing to be tied to this theory, that the gelling of the binder can be attributed to the loss of monovalent copper ions ($Cu^+$) from the copper-containing metallic effect pigments. These monovalent copper ions are thought subsequently to undergo transition, with loss of an electron, into the more stable divalent state ($Cu^{2+}$). As a result of this, binder is reduced, and as a result of that there is crosslinking of binder and hence a gelling and the unwanted increase in viscosity.

The inventors further suppose that, owing to the high specific surface area, i.e., surface area per unit weight, the copper-containing metallic effect pigments for use in accordance with the invention exhibit a very large area of contact with surrounding binder. The large contact area is thought to result in increased loss of copper ions into the binder. The high specific surface area is a consequence of the narrow thickness distribution with an $h_{50}$ from a range from 10 to 100 nm, in particular with an $h_{50}$ from a range from 10 to 50 nm, and an $h_{90}$ from a range from 20 to 150 nm, more particularly in the case of an $h_{90}$ from a range from 20 to 70 nm. The lower the thickness of the copper-containing metallic effect pigments, the greater the gelling of the binder. The platelet-shaped, copper-containing metallic effect pigments for use in accordance with the invention are therefore metallic effect pigments which have an extremely low thickness and hence a high specific surface area.

With nonleafing platelet-shaped, copper-containing metallic effect pigments in particular there is rapid gelling of the binder, since nonleafing copper-containing metallic effect pigments are surrounded by binder completely, i.e., both the top pigment surface and the bottom pigment surface. In the case of nonleafing copper-containing metallic effect pigments, therefore, copper ions can be lost via the top surface and the bottom surface.

In the case of leafing copper-containing metallic effect pigments, the loss of copper ions is less, since leafing metallic effect pigments float and therefore the top surface comes into contact only to a small extent, or not at all, with the binder. Where leafing copper-containing metallic effect pigments exhibit nonleafing behavior, as a result of additives, such as citric acid, for example, the problem of increased loss of copper ions likewise occurs.

The effect according to the invention, i.e., the inhibition of the gelling of a coating composition comprising copper-containing metallic effect pigments, is also apparent in the case of copper-containing, platelet-shaped PVD metallic effect pigments which, on account of a low metallic effect pigment thickness, have a high specific opacity and therefore a large surface area in contact with binder. The present invention therefore extends likewise to copper-containing PVD metallic effect pigments, such as PVD brass effect pigments, for example, insofar as their thicknesses exhibit the thickness distributions that are addressed in this specification. All data in this application therefore relate to copper-containing, platelet-shaped metallic effect pigments obtained by milling, and to copper-containing PVD metallic effect pigments, insofar as their thickness distribution(s) match(es) with those of the present specification.

The gelling of binder significantly reduces the shelf life of a coating composition which comprises the mixture of copper-containing, platelet-shaped metallic effect pigments for use in accordance with the invention. On contact between the platelet-shaped, copper-containing metallic effect pigments for use in accordance with the invention and binder, there may be gelling, and hence an increase in viscosity, within just 24 hours.

Surprisingly, the gelling of binder can be suppressed, and preferably prevented, if the platelet-shaped, copper-containing metallic effect pigments used in accordance with the invention are present in a mixture with at least one component which is a cellulose derivative selected from the group consisting of alkylcellulose, hydroxyalkylcellulose, alkyl(hydroxy-alkyl)cellulose, and mixtures thereof, and/or at least with one additive having antioxidative and/or radical-inhibiting properties.

By shelf life is meant a consistent viscosity or a small increase in viscosity, and consistent optical qualities of the paint when properly stored within this period of time. In accordance with the invention, the shelf life is preferably at least 6 or 12 months at room temperature.

The at least one component which is a cellulose derivative selected from the group consisting of alkylcellulose, hydroxyalkylcellulose, alkyl(hydroxy-alkyl)cellulose, and mixtures thereof is added preferably in the range from 0.1% to 40% by weight, more preferably from 0.5% to 20% by weight, preferably from 1% to 10% by weight, even more preferably from 1% to 5% by weight, based in each case on the total weight of the preparation—paint or printing ink, for example.

The at least one component which is at least one additive having antioxidative and/or radical-inhibiting properties is added preferably in the range from 1% to 15% by weight, more preferably from 3% to 10% by weight, based in each case on the weight of the metallic effect pigment used.

An additive having antioxidative and/or radical-inhibiting properties acts principally chemically by protecting the copper-containing metallic effect pigment from oxidative influences by oxidation of the additive having antioxidative properties. An additive having radical-inhibiting properties, such as a radical scavenger, for example, acts by scavenging electrons given off by copper ions, in the oxidation, for example, of monovalent copper ($Cu^+$) to divalent copper ($Cu^{2+}$).

The mode of operation of the additive having antioxidative and/or radical-inhibiting properties cannot be unambiguously assigned, since the antioxidative properties and the radical-inhibiting properties may apply separately from one another or else together.

In accordance with another preferred embodiment of the invention there is in the mixture, in addition to the at least one further component, a corrosion inhibitor present.

A corrosion inhibitor acts principally physically, by isolating the copper-containing metallic effect pigment from the surrounding medium, such as the binder of a coating composition, for example. On the one hand this suppresses, and preferably prevents, the oxidation of copper to monovalent copper ($Cu^+$). On the other hand, the loss of copper ions to the surrounding medium is also suppressed, and preferably prevented.

A combination which has emerged as being very effective is that of a cellulose derivative selected from the group consisting of alkylcellulose, hydroxyalkyl-cellulose, alkyl(hydroxyalkyl)cellulose, and mixtures thereof with at least one additive having antioxidative and/or radical-inhibiting properties, for the protection of platelet-shaped, copper-containing metallic effect pigments or of platelet-shaped, copper-containing metallic effect pigment-containing coating compositions.

A combination which has also emerged as being very effective is that of a cellulose derivative selected from the group consisting of alkylcellulose, hydroxyalkylcellulose, alkyl(hydroxyalkyl)cellulose, and mixtures thereof with at least one corrosion inhibitor, for the protection of platelet-shaped, copper-containing metallic effect pigments or of platelet-shaped, copper-containing metallic effect pigment-containing coating compositions.

A further combination which has emerged is that of at least one additive having antioxidative and/or radical-inhibiting properties with at least one corrosion inhibitor for the protection of platelet-shaped, copper-containing metallic effect pigments or of platelet-shaped, copper-containing metallic effect pigment-containing coating compositions.

A combination which has emerged as being very suitable is that of a cellulose derivative selected from the group consisting of alkylcellulose, hydroxyalkylcellulose, alkyl(hydroxyalkyl)cellulose, and mixtures thereof, at least one additive having antioxidative and/or radical-inhibiting properties, and at least one corrosion inhibitor for protecting platelet-shaped, copper-containing metallic effect pigments or platelet-shaped, copper-containing metallic effect pigment-containing coating compositions.

The shelf life in the case of a coating composition of the invention is preferably at least 6 months, preferably at least 12 months at room temperature, i.e., in a temperature range from about 15 to about 30° C., preferably from about 18 to about 25° C. A shelf life of 10 weeks at 40° C. corresponds approximately to a shelf life of 6 months at 25° C.

By shelf life is meant that a coating composition, such as a printing ink, when stored properly at 25° C., for example, does not undergo any visual change and, irrespective of any—preferably slight—rise in viscosity, can readily be reagitated and can therefore be used as intended.

A storage-stable coating composition can be readily agitated by stirring, where appropriate with addition of organic solvent, so that the platelet-shaped copper-containing metallic effect pigments are dispersed and the coating composition can be used as intended as a paint, varnish or printing ink, for example.

In accordance with one preferred development of the invention, the copper-containing metallic effect pigments have a thickness distribution, determined via thickness counting by scanning electron microscopy (SEM) and represented as cumulative undersize distribution,
a) with an $h_{50}$ of 10 to 50 nm,
b) with an $h_{90}$ of 20 to 70 nm.

On account of their very low average thickness, the platelet-shaped, copper-containing metallic effect pigments for use in accordance with the invention possess a very high opacity. The less the average thickness of the copper-containing metallic effect pigments, the greater the opacity.

Opacity or hiding power of a pigment is a term typically used to identify the coverage of an area per unit weight of pigment amount. The less the average thickness of the pigments, the greater the area covered by the pigment and therefore its opacity.

Very thin metallic effect pigments with a very narrow thickness distribution stack more uniformly in the application medium than metallic effect pigments having a broad thickness distribution. With the conventional metallic effect pigments there may easily be disuniformities in the stacking of the pigments in the application medium. Thus, in particular, very thick metallic effect pigments may act as "spacers", which detract from the orientation of the surrounding or adjacent pigments in the application medium. This adversely affects luster, flop, and, in certain circumstances, the hiding power of the metallic effect pigments. It has a particularly deleterious effect in printing applications. In comparison to coatings, prints have a substantially lower film thickness and a lower binder fraction.

Determining the precise average thickness of platelet-shaped metallic pigments is difficult. In practice, the pigment thickness is determined via the degree of water covering (spreading according to DIN 55923) or by scanning electron microscopy (SEM). With the area of water covering it is possible to calculate only an average thickness h of the pigments, but not the thickness distribution. In order to determine the thickness distribution as well, the average thickness of the metallic effect pigments for use in accordance with the invention was determined, for the purposes of this invention, by means of scanning electron microscopy (SEM). With this method, measurement should encompass a sufficient number of particles to allow a representative statistical evaluation to be performed. Typically about 50 to 100 particles are measured.

The thickness distribution is usefully represented in the form of a cumulative undersize distribution or cumulative frequency distribution. An appropriate average is the $h_{50}$ of the cumulative undersize distribution or of the cumulative frequency distribution. A measure of the coarse fraction is the $h_{90}$ FIGURE. It states that 90% of all of the pigment particles have a thickness equal to this FIGURE and/or below this FIGURE. Correspondingly, for example, an $h_{98}$ says that 98% of all of the pigment particles have a thickness equal to this FIGURE and/or below this FIGURE. Similarly, the $h_{10}$ is a measure of the fine fraction of the thickness distribution, and says that 10% of all the pigment particles have a thickness equal to this FIGURE and/or below this FIGURE.

These values may be determined arithmetically from a list of the individual measurement values, with the aid, for example, of the "quantile" function in an Excel representation.

Determining the thicknesses of the individual pigments by means of SEM is done in accordance with the method described in DE 103 15 775 A1.

In the result of the thickness count by scanning electron microscopy ($h_{50}$ of the cumulative undersize distribution or cumulative frequency distribution), for the copper-containing metallic effect pigments for use in accordance with the invention, such as gold bronze pigments, for example, an average thickness $h_{50}$ of 10 to 100 nm, more preferably 10 to 50 nm, very preferably of 15 to 45 nm, with particular preference of 15 to 40 nm, and very preferably of 20 to 35 nm, was found.

Below an average thickness $h_{50}$ of 10 nm, the resulting hues of the copper-containing metallic effect pigments become too dark, attributable to a reduction in the reflectance with retention of the high absorption properties of the copper or brass. Owing to the increasing transparency of the copper-containing metallic effect pigments, there is also a reduction in opacity, and unwanted shifts in hue may come about.

Above an average thickness $h_{50}$ of 50 nm, advantageous optical properties were only present in a greatly attenuated form in the copper-containing metallic effect pigments for use in accordance with the invention.

Outside of a range with an average thickness $h_{50}$ of 10 to 50 nm, copper-colored metallic effect pigments were obtained which have a gold color but no longer exhibit a mirror effect. These pigments are used preferably in applications where no mirror gloss is desired or necessary, such as, for example, when a printing ink is applied to an absorbent substrate, such as to paper, for example.

Furthermore, the copper-containing metallic effect pigments for use in accordance with the invention have a thickness distribution, determined via thickness counting by scanning electron microscopy (SEM), with an $h_{90}$ of 20 to 150 nm, preferably of 20 nm to 80 nm, more preferably of 20 nm to 70 nm, very preferably of 20 to 60 nm, even more preferably of 21 to 50 nm, and with particular preference of 22 to 40 nm.

Above an $h_{90}$ of 70 nm, the advantageous properties of the metallic effect pigments for use in accordance with the invention were no longer observable. In particular it was no longer possible to ascertain a clear mirror in the case of a film reverse application (with very good distinctness of image).

Platelet-shaped, copper-containing metallic effect pigments having an $h_{90}$ of below 20 nm were not hitherto producible by means of milling.

It is thought that the advantageous optical properties of the metallic effect pigments for use in accordance with the invention derive from a very low thickness of all the pigments in the pigment thickness distribution. The $h_{98}$ ought therefore to be preferably in the range from 21 nm to 200 nm, preferably from 21 nm to 90 nm, more preferably from 21 to below 80 nm, with particular preference from 24 to 70 nm, and with very particular preference from 25 to 60 nm.

The low thicknesses of the copper-containing metallic effect pigments for use in accordance with the invention have the advantageous effect of a very good orientation of the pigments in the application medium, as for example in a printing ink, especially in a gravure ink or flexographic ink for producing gold-colored film reverse applications.

It is thought that, below a defined platelet thickness, these platelets are so flexible that they conform perfectly to the substrate. This effect is well established for PVD aluminum pigments, and is exploited especially in the film reverse applications.

In a further-preferred embodiment of the invention, the metallic effect pigments for use in accordance with the invention have an $h_{10}$ of the thickness distribution in the range from 8 to 50 nm, preferably from 8 to 25 nm, and more preferably from 10 to 20 nm. Below an $h_{10}$ of 8 nm the pigments are too thin, leading to impaired optical properties. At an $h_{10}$ above 25 nm, the copper-containing metallic effect pigments no longer exhibit a mirror effect, but instead only exhibit a gold-colored appearance.

Furthermore, the metallic effect pigments for use in accordance with the invention have a relative breadth of the thickness distribution $\Delta h$, which is determined via thickness counting by scanning electron microscopy (SEM) and is calculated from the corresponding cumulative undersize curve of the relative frequency or cumulative frequency distribution of the relative frequency in accordance with the formula $$\Delta h = 100 \times (h_{90} - h_{10})/h_{50},$$

of 30% to 100%, preferably of 30% to 90%, more preferably of 35% to 85%, and very preferably of 40% to 80%.

In view of the narrow thickness distribution, similar to that of PVD metallic effect pigments, surprisingly, of the pigments for use in accordance with the invention that are produced by wet milling, these pigments are similar in their optical properties to PVD pigments, but can be produced in a substantially more cost-effective way and with satisfactory hue stability.

In terms of longitudinal extent, the metallic effect pigments for use in accordance with the invention, produced in particular by wet milling of copper or brass powder, are not fundamentally different from commercially traded gold bronze pigments produced by dry milling of copper or brass powder. Specifically, the pigment sizes are dependent on the intended use.

The copper-containing metallic effect pigments for use in accordance with the invention preferably have an average size $d_{50}$ of 3 to 50 µm, more preferably of 4 to 30 µm, with particular preference of 5 to 20 µm, and very preferably of 6 to 15 µm.

The longitudinal extent d (diameter) is determined in laser diffraction experiments on the basis of the Fraunhofer diffraction and/or Mie scattering theory. The evaluation of the diffraction data is based on a model which is geared to the diameter of an equivalent sphere. For this reason, the values obtained are not absolute, but the diameters measured have become established as reliable relative values in the description of the size characteristics of platelet-shaped metallic pigments.

The $d_{50}$ of the pigment length corresponds to 50% of the cumulative undersize distribution curve or cumulative frequency distribution, measured and evaluated in the form of a volume distribution of equivalent spheres.

Entirely surprisingly it has been found that the coating compositions pigmented with the copper-containing metallic effect pigments having an $h_{50}$ in the range from 10 to 50 nm and an $h_{90}$ in the range from 20 to 70 nm exhibit, in "film reverse applications", a gold-colored and mirrorlike effect which it was not hitherto possible to realize with conventional copper-containing metallic effect pigments produced by dry milling.

By a "film reverse application" is meant that a printing ink pigmented with metallic effect pigments is printed onto a transparent film. The print cured on the film, when copper-containing metallic effect pigments for use in accordance with the invention are used, produces a golden (gold-colored) mirrorlike effect when viewed from the reverse. This mirror effect comes about as a result of the fact that at least some of the copper-containing metallic effect pigments of the invention, because of their low thickness and their narrow thickness distribution, are oriented preferably directly at the film surface. The fraction of the copper-containing metallic effect pigments of the invention arranged at or along the film surface produces the extraordinary mirror luster. The further copper-containing metallic effect pigments of the invention that are disposed in the application medium—the printing ink, for example—are essential for hiding, i.e., opacity.

The platelet-shaped, copper-containing metallic effect pigments for use in accordance with the invention are metallic effect pigments which have a copper content of at least 60% by weight, based on the total metal content of the pigments.

The copper-containing metallic effect pigments for use in accordance with the invention comprise, in particular, copper pigments and also brass pigments comprising zinc and copper (gold bronzes).

The copper effect pigments preferably have a copper content of 98% to 100% by weight, and more preferably of 99% to 99.999% by weight, based in each case on the total metal content of the pigments. It will be appreciated that the skilled person reads the indication "100% by weight" copper to include extraneous metals possibly present in trace amounts.

The brass effect pigments, commonly referred to as "gold bronzes", preferably have a copper content of 70% to less than 100% by weight, more preferably 75% to 90% by weight. The zinc content, correspondingly, is preferably between 30% and 10% by weight, and up to 2% by weight, preferably below 1% by weight, of impurities in the form of other metals may be present. With brass effect pigments or gold bronze effect pigments, the hue is determined by the copper/zinc ratio of the alloy. Gold bronze effect pigments trade, in characteristic natural hues, as "pale gold", with a copper fraction of around 90% by weight, remainder around 10% by weight zinc; as "rich pale gold", with a copper fraction of around 85% by weight, remainder around 15% by weight zinc; and as "rich gold", with a copper fraction of around 70% by weight, remainder around 30% by weight zinc. The FIGUREs in % by weight here are based on the total metal content of the pigment.

In one preferred embodiment, the brass effect pigments comprise an "impurity" with, for example, 0.1% to 2% by weight, preferably 0.5% to 2% by weight, of aluminum, based on the total metal content of the metallic effect pigment. Alloys of this kind have proven more stable to corrosion as compared with brass effect pigments containing exclusively copper and zinc.

The platelet-shaped, copper-containing metallic effect pigments for use in accordance with the invention may exhibit leafing behavior (leafing pigments) or nonleafing behavior (nonleafing pigments).

By nonleafing metallic effect pigments is meant in accordance with the invention that the metallic effect pigments predominantly undergo arrangement in an application medium, as for example a printing ink, paint or varnish, and so the metallic effect pigments are completely surrounded by the application medium. Over the thickness of an applied film of an application medium, therefore, the nonleafing metallic effect pigments are in a distributed arrangement, in largely plane-parallel arrangement with respect to the surface of the substrate.

By leafing metallic effect pigments is meant in accordance with the invention that the metallic effect pigments undergo arrangement predominantly at an interface (surface) or in the vicinity of an interface of an application medium, as for example of a printing ink, paint or varnish, and so the metallic effect pigments are not fully surrounded by the application medium, the contact between metallic effect pigment and application medium instead being predominantly only via one surface of the metallic effect pigment.

The nonleafing behavior of copper-containing metallic effect pigments can also be induced by addition of additives, such as citric acid, for example. In this way, originally leafing copper-containing metallic effect pigments may become nonleafing metallic effect pigments.

As a driving force for plane-parallel orientation of metallic effect pigments, in addition to the interface-chemical incompatibility of the pigments with the binder system, the form factor is another important characteristic for the properties of the copper-containing metallic effect pigments for use in accordance with the invention.

The form factor f is understood to be the ratio of the average longitudinal extent to the average thickness of the pigment platelets.

The dimensionless form factor f in this invention is defined as:

$$f = 1000 * \frac{d_{50}\ (\mu m)}{h_{50(nm)}}$$

The copper-containing metallic effect pigments for use in accordance with the invention, gold bronze pigments for example, preferably have a form factor f of 30 to 3000, more preferably of 150 to 3000. The pigments of the invention are preferably characterized by a form factor f of 250 to 2500, more preferably of 300 to 1000, and very preferably of 325 to 600.

In the case of prints, the binder fractions and the film thicknesses are generally very much lower than in coatings. This is especially true of gravure inks. Gravure inks pigmented with commercially traded gold bronze pigments have a solids content of around 40% by weight. Printed films of such inks have a wet film thickness of around 3 to 6 μm and a dry film thickness of around 1.5 to 3 μm. In the case of gravure inks pigmented with PVD pigments, the solids fractions are around 5% to 20% by weight of the total gravure ink. The associated dry film thicknesses are only 0.5 to 1.5 μm. At these extremely low film thicknesses, largely uniform plane-parallel orientation of the metallic pigments is necessary. This has hitherto been achievable only with PVD metallic effect pigments.

Print applications pigmented with the copper-containing metallic effect pigments for use in accordance with the invention, especially film reverse applications, have optical effects (in respect of luster/mirror), on account of the low average particle thickness and narrow particle thickness distribution of the metal effect pigments used, that are comparable with those of print applications pigmented with conventional PVD metallic effect pigments.

The platelet-shaped, copper-containing metallic effect pigments used preferably in the mixture according to the invention are metallic effect pigments which are obtained by milling with grinding media. Unlike PVD metallic effect pigments, metallic effect pigments obtained using grinding media do not have an absolutely planar surface, but instead a surface which exhibits depressions and elevations. Furthermore, the marginal region of metallic effect pigments obtained by PVD processes and metallic effect pigments obtained by milling is significantly different. In the case of PVD pigments, the marginal region has relatively linear fracture edges. The marginal region of copper-containing metallic effect pigments obtained by milling and/or deformation is irregularly shaped or frayed, and in general also has fissures or gaps.

According to another preferred embodiment, the at least one additive is an antioxidant and/or radical scavenger.

It is further preferred for the at least one additive to be an additive mixture which comprises at least two different additives selected from the group consisting of antioxidant and/or radical scavenger and corrosion inhibitor.

The additive mixture used in the context of the present invention therefore encompasses preferably the following combinations:
  antioxidant and corrosion inhibitor;
  radical scavenger and corrosion inhibitor;
  antioxidant and radical scavenger;
  antioxidant, radical scavenger, and corrosion inhibitor,
each of which is used optionally in combination with a cellulose derivative selected from the group consisting of alkylcellulose, hydroxyalkylcellulose, alkyl(hydroxyalkyl)cellulose, and mixtures thereof.

According to one preferred variant of the invention, the corrosion inhibitor, also referred to as a passivating inhibitor, is selected from the group consisting of fatty acids, carboxylic acid derivatives, organic phosphates and phosphonates and their esters, organically functionalized silanes, aliphatic or cyclic amines, aliphatic and aromatic nitro compounds, oxygen-, sulfur- or nitrogen-containing heterocycles, sulfur/nitrogen compounds of higher ketones, aldehydes and alcohols, thiols, beta-diketones, beta-keto esters, and mixtures thereof.

According to one preferred embodiment, carboxylic acid derivatives are particularly preferred as corrosion inhibitors. According to one very preferred variant, the carboxylic acid derivatives are a partial ester of a dicarboxylic acid, tricarboxylic acid, tetra-carboxylic acid, or of a mixture thereof.

The preferred dicarboxylic acids are dicarboxylic acids having 3 to 20 C atoms, preferably 4 to 8 C atoms, and are present preferably in the form of monoesters.

The dicarboxylic acids are selected preferably from the group consisting of malonic acid, succinic acid, glutaric acid, adipic acid, pimelic acid, suberic acid, azelaic acid, sebacic acid, maleic acid, fumaric acid, sorbic acid, phthalic acid, terephthalic acid, dodecanedioic acid, tetradecanedioic acid, hexadecanedioic acid, and mixtures thereof. Preference is given to using succinic acid.

Succinic monoester has proven very suitable.

The preferred tricarboxylic acids are tricarboxylic acids having 6 to 20 C atoms, preferably 8 to 12 C atoms.

The tricarboxylic acids are preferably selected from the group consisting of 1,2,3-propanetricarboxylic acid, citric acid, hemimellitic acid, trimellitic acid, trimesic acid, and mixtures thereof.

The preferred tetracarboxylic acids are tetracarboxylic acids having 10 to 20 C atoms.

By way of example, pyromellitic acid can be used.

The aforementioned carboxylic acids are preferably partially esterified with alcohols having 1 to 12 carbon atoms. Particularly preferred are methanol, ethanol, n-propanol, isopropanol, n-butanol, sec-butanol, isobutanol, amyl alcohol, isoamyl alcohol, 1-hexanol, 2-hexanol, 3-hexanol, cyclohexanol, and mixtures thereof.

It is preferred for the partially esterified dicarboxylic, tricarboxylic and/or tetracarboxylic acids to possess at least one free carboxyl group, via which attachment to the copper-containing metallic effect pigment surface can be made.

It is of course also possible to use mixtures of dicarboxylic, tricarboxylic, and tetracarboxylic acid, preferably of the respective partial esters.

In accordance with the invention it is possible, furthermore, as corrosion inhibitors to use the following:
  Organically modified phosphonic acids and/or their esters of the general formula R—P(O) (OR$_1$) (OR$_2$), where: R=alkyl, aryl, alkylaryl arylalkyl, and also alkyl ethers, especially ethoxylated alkyl ethers, and R$_1$, R$_2$=H, C$_n$H$_{2n+1}$, with n=1-6, it being possible for alkyl in each case to be branched or unbranched. R$_1$ may be the same as or different from R$_2$.
  Organically modified phosphoric acids and esters of the general formula R—O—P(OR$_1$) (OR$_2$), where: R=alkyl, aryl, alkylaryl arylalkyl, and also alkyl ethers, especially ethoxylated alkyl ethers, and R$_1$, R$_2$=H, C$_n$H$_{2n+1}$, with n=1-6, it being possible for alkyl in each case to be branched or unbranched. R$_1$ may be the same as or different from R$_2$.

Use may be made of pure phosphonic acids or esters or phosphoric acids or esters, or of any desired mixtures thereof.

The passivating inhibitor layer may further consist of or comprise corrosion-inhibiting, organically functionalized silanes, aliphatic or cyclic amines, aliphatic or aromatic nitro compounds, or heterocycles containing oxygen, sulfur and/or nitrogen. In this context, according to one preferred variant of the invention, nitrogen-containing heterocyclic compounds are used. Particular preference is given to triazoles, and very particular preference to benzotriazoles. These triazoles and benzotriazoles may be unsubstituted or substituted, with, for example, one or more alkyl groups having 1 to 12 C atoms, preferably 2 to 6 C atoms.

Additionally it is possible to make use, for example, of thiourea derivatives, sulfur compounds and/or nitrogen compounds of higher ketones, aldehydes, and alcohols, such as fatty alcohols, or thiols or mixtures thereof.

The passivating inhibitor layer may also be composed of the aforementioned substances. Where amine compounds are used, these compounds contain preferably organic radicals having more than 6 C atoms, preferably having to 24 C atoms, more preferably having 10 to 18 C atoms. These amines are used preferably together with organic phosphonic acids and/or phosphoric esters, preferably as specified above, or mixtures thereof.

According to one further preferred variant, the antioxidant and/or the radical scavenger is selected from the group consisting of phenols, phenol derivatives, particularly alkylhydroxytoluene such as butylated hydroxytoluene, dialkylhydroxytoluene preferably 2,6-di-tert-butyl-p-cresol, and quinones, quinone derivatives, nitroso compounds, nitrones, vitamin C, vitamin C derivatives, vitamin E, vitamin E derivatives, and mixtures thereof.

The additives used preferably in accordance with the present invention belong on the one hand to the class of the corrosion inhibitors, such as carboxylic esters and carboxylic monoesters, for example, and also triazole derivatives, and on the other hand to the class of the antioxidants and radical inhibitors, such as phenol derivatives, vitamin C and E, for example, or quinones and quinone derivatives. These additives have proven very suitable as an addition to coating compositions, more particularly as an addition for printing inks. Printing inks which comprise the platelet-shaped, copper-containing metallic effect pigments for use in accordance with the invention and also comprise at least one of the aforementioned additives have a significantly extended shelf life.

Particularly preferred is a combination of the aforementioned additives, since in that case there is not only an antioxidative and/or radical-inhibiting effect but also a corrosion-inhibiting effect.

According to a further preferred embodiment of the invention, the corrosion inhibitor envelops the platelet-shaped, copper-containing metallic effect pigment. The corrosion inhibitor may be an enveloping inorganic-chemical coating, organic-chemical coating or inorganic/organic-chemical coating.

Anticorrosion layers which ensure particularly effective corrosion control for the metallic effect pigments for use in accordance with the invention comprise or consist of silicon oxide, preferably silicon dioxide, zirconium oxide, cerium oxide, aluminum oxide, polymerized polymeric resins, phosphates, phosphites, borates or mixtures thereof.

Preference is given to silicon dioxide layers, the silicon dioxide surface being coated preferably with silanes.

The $SiO_2$ layers are produced preferably by sol-gel processes, with average layer thicknesses of 2 to 150 nm and preferably of 5 to 40 nm, in organic solvents.

According to a further variant of the invention, the copper-containing metallic effect pigments may have a metal oxide layer for corrosion control, the metal of the metal oxide layer being of the same kind as the metal of the metallic effect pigment.

Oxide layers of this kind are also known from typical copper or gold bronze effect pigments.

These oxide layers are obtained by oxidizing treatments. On account of their intrinsic colors and on account of interference effects, these metal oxide layers, depending on their layer thickness, produce effect pigments in any of a wide variety of hues in the yellow-red color range. The base color of the metallic effect pigment also plays a large part here, of course.

In the course of the oxidation, part of the metal is always converted to the corresponding oxide. Hence it is preferred not to use, for oxidation, the extremely thin metallic effect pigments for use in accordance with the invention. Such pigments would have only a very low remaining metal content, or none at all, and that would have great disadvantages in relation to their opacity. For oxidation, therefore, it is preferred to use metallic effect pigments having average thickness $h_{50}$ in the range from 25 to 50 nm or, preferably, in the range from 50 to 100 nm.

In the oxidizing treatment of copper-containing metallic effect pigments, atmospheric oxygen acts on the copper-containing metallic effect pigment over a defined period of time at a defined temperature, and forms a thin layer of oxide on the copper-containing metal platelets. Interference reflection evokes interesting color shades. Oxidized, copper-containing metallic effect pigments are traded in hues which include English green, lemon, ducat gold and flame red shades.

In the invention, therefore, it is also possible to use copper-containing metallic effect pigments that have been oxidized and thereby protected with respect to corrosion.

According to one variant of the invention, the mixture comprises cellulose derivatives selected from the group consisting of alkylcellulose, hydroxyalkylcellulose, alkyl(hydroxyalkyl)cellulose, and mixtures thereof.

The alkylcellulose and/or hydroxyalkylcellulose and/or alkyl(hydroxyalkyl)cellulose preferably have one or more alkyl radicals and/or hydroxyalkyl radicals and/or alkyl(hydroxyalkyl) radicals each independently of one another having 1 to 8, preferably 2 to 6, C atoms. The alkyl radical may also be a cycloalkyl radical.

Having emerged as being very suitable in this context are, in particular, methylcellulose, ethylcellulose, propylcellulose, (hydroxyethyl) cellulose, (hydroxy-propyl)methylcellulose, ethyl(hydroxyethyl)cellulose, benzylcellulose, carboxymethylcellulose or mixtures.

Particular preference is given to using ethylcellulose. It has surprisingly emerged that ethylcellulose, for reasons which are not yet understood, has a particularly stabilizing effect. Hence ethylcellulose allows the provision of storage-stable mixtures of the invention and of coating compositions of the invention.

Besides the aforementioned cellulose derivatives, it is of course also possible for further cellulose esters, cellulose ethers, and mixtures thereof to be present in the mixture of the invention or in the coating composition of the invention.

Cellulose esters which have emerged as being very suitable include cellulose acetate, cellulose acetobutyrate, cellulose propionate, cellulose acetopropionate or mixtures thereof.

A mixture according to the invention of platelet-shaped, copper-containing metallic effect pigments with at least one additive having antioxidative and/or radical-inhibiting properties and with cellulose ether, more particularly ethylcellulose, is a particularly preferred embodiment of the invention. This mixture is outstandingly suitable for direct incorporation into inks, especially printing inks or printing-ink concentrates. It is further preferred for the aforementioned mixture according to the invention further to comprise a corrosion inhibitor.

The use of ethylcellulose allows the provision of a mixture with organic solvent or organic solvent mixture.

An organic solvent mixture may in accordance with the invention, besides organic solvent, also contain water in an amount of 0% to 10%, preferably of 1% to 8%, more preferably of 2% to 5%, by weight, based in each case on the total weight of solvent. Very preferably the water content of the organic solvent is less than 2% by weight, based on the total weight of solvent. It is therefore preferred to use technical organic solvents which may have a residual water content.

Since printing inks of particular brilliance are solvent borne, i.e., comprise organic solvent, the use of ethylcellulose, which is a binder, allows the provision of a precursor product or concentrate that can be used directly to produce printing inks. The printing inks provided using ethylcellulose have an extraordinary stability, i.e., low tendency toward gelling.

According to one further-preferred embodiment, the mixture comprises an organic solvent or organic solvent mixture.

Suitable solvents are alcohols, examples being methanol, ethanol, 1-propanol, 2-propanol or mixtures thereof. It is also possible to use substituted alcohols, such as alkoxy alcohols, for example, where the alkoxy radical and the alcohol radical may independently of one another have 1 to 4, preferably 2 to 3, C atoms. Ethoxypropanol and/or methoxypropanol have proven very suitable. As solvents it is also possible to use esters, preferably carboxylic acid alkyl esters, where the carboxylic acid radical and the alkyl radical may independently of one another have 1 to 4, preferably 2 to 3, C atoms. Ethyl acetate, isopropyl acetate, n-propyl acetate and/or n-butyl acetate have proven very suitable.

It is of course also possible to use mixtures of different solvents. Such a mixture may be, for example, a mixture of ethanol and esters such as ethyl acetate or n-propyl acetate.

According to one preferred embodiment, the coating composition is a printing ink, a printing ink concentrate, a varnish, a varnish concentrate, a paint or a paint concentrate.

The coating composition of the invention is preferably in a compacted form, preferably as pellets, granules, tablets, briquettes and/or sausages. According to a further preferred variant, the mixture as described herein may likewise be in a compacted form, preferably as pellets, granules, tablets, briquettes and/or sausages. The remarks below therefore apply not only to the inventive mixture as described herein but also to the inventive coating composition as also described herein.

A further preferred embodiment relates to the use of a mixture of platelet-shaped, copper-containing metallic effect pigments as described herein in a coating composition which is preferably in compacted form.

According to one preferred embodiment, the mixture according to the invention or the coating composition of the invention takes the form of a paste like product.

The solids content of these pastes comprising the copper-containing metallic effect pigments is situated preferably in a range from 30% to 90%, more preferably 40% to 75%, and very preferably 45% to 70%, by weight, based in each case on the total weight of the paste.

According to one preferred development, the mixture according to the invention or the coating composition of the invention is present in a low-solvent or solvent-free form. With further preference the mixture according to the invention or the coating composition of the invention is present in a low-dust, preferably dust-free, presentation form.

A low-solvent or solvent-free presentation form can be obtained by drying a solvent-containing mixture according to the invention, as described herein, or a solvent-containing coating composition as also described herein, to give a dry or largely dry powder, preferably a stabilized, copper-containing metallic effect pigment powder.

The dry or dried, copper-containing metallic effect pigment powder can be processed further by addition of—preferably organic—solvent, preferably of less than 15%, more preferably of 1% to 11%, even more preferably of less than 10%, more preferably still of 3% to 8%, by weight, based in each case on the total weight of the preparation, in a suitable homogenizer to give a nondusting metal powder, preferably in compacted form. Compacting may be brought about by pelletizing, granulating, tableting, briquetting, extruding, etc.

It is of course also possible first of all, by filtering a preparation, as for example a dispersion such as a paste, to obtain a filtercake, and then to dry this filtercake and subsequently paste it up again with a different solvent (rewetting).

Surprisingly, the copper-containing metallic effect pigments for use in accordance with the invention may, however, also be converted into granules, pellets, briquettes, tablets or sausages by adding a resin dispersion to a filtercake.

These presentation forms possess the advantages that they do not dust, they have easy metering qualities, and they are outstandingly dispersible.

The mixtures according to the invention can therefore be provided very advantageously indeed in compacted form, as for example as granules, pellets, tablets, briquettes, sausages, etc., with high levels of copper-containing metallic effect pigment—for example, from 95% to 35%, preferably from 90% to 35%, more preferably from 85% to 65%, and very preferably 70% to 40%, by weight, based in each case on the total weight of compacted form. The residual moisture content, i.e., the amount of—preferably organic—solvent in this case is situated preferably in a range from 0% to 15%, preferably from 1% to 11%, more preferably from 3% to 8%, by weight, based in each case on the total weight of compacted form.

On account of the high specific surface area of the copper-containing metallic effect pigments for use in accordance with the invention, it is necessary to use relatively large quantities of dispersing resin for the purpose, for example, of their compacting—for example, pelletizing, tableting, briquetting, granulating, etc. It is preferred to use 2% to 50% by weight, more preferably 5% to 30% by weight, of resin, based on the overall formulation of the compacted form, for example, pellets, tablets, briquettes, sausages, granules, etc.

There are a large number of dispersing resins that can be used for compacting—for example, pelletizing, tableting, briquetting, granulating, etc. Examples of such resins include both naturally occurring resins and synthetic resins or mixtures thereof. They encompass, for example, alkyd resins, carboxymethylcellulose and carboxyethylcellulose resins, cellulose acetate, cellulose acetate propionate (CAP) and cellulose acetate butyrate (CAB), cumarol-indene resins, epoxide esters, epoxide-melamine and epoxide-phenol condensates, ethylcellulose and/or methylcellulose, ethylhydroxyethylcellulose, hydroxyethylcellulose, hydroxypropylmethylcellulose, ketone resins and/or maleic acid resins, rosins, melamine resins, phenolic and/or modified phenolic resins, polyacrylamide, polycarbonate, polyimide, polyester, polyether, polyurethane and/or vinyl resins, and mixtures thereof.

Among these polymeric resins, the following resins are particularly suitable: acrylate copolymers and/or acrylic ester resins, polyacrylonitrile and/or acrylonitrile copolymer resins, copolymers of butadiene and vinylidene chloride, butadiene/styrene copolymers, methyl acrylate and/or methyl methacrylate copolymers; and also polybutene, polyisobutylene, polyvinyl acetate, polyvinyl alcohol, polyvinyl chloride, polyvinyl ether, polyvinylpyrrolidone and/or polystyrene resins. Further copolymers constitute styrene/maleic anhydride and/or styrene/shellac resins, vinyl chloride/vinyl acetate resins, vinyl chloride/vinyl ether resins and/or vinyl chloride/vinylidene chloride resins, and mixtures thereof.

Use may also be made in accordance with the invention, furthermore, of naturally occurring resins such as gum Arabic, gutta percha, casein, gelatin, and mixtures thereof.

Preference is given to aldehyde resins, such as the Laropal series from BASF AG, Ludwigshafen. Moreover, waxes are among binder materials contemplated. Examples here include natural waxes such as beeswax, candelilla wax, carnauba wax, montan wax, and also paraffin waxes, or mixtures thereof. Synthetic waxes such as PE waxes, for example, are also suitable.

With particular preference the coating composition is a printing ink or a printing ink concentrate.

Printing inks of the invention based on platelet-shaped, copper-containing metallic effect pigments, as specified above, may be used with advantage across a multiplicity of printing application, such as gravure printing or digital printing, for example. With the printing inks of the invention, brilliant gold effects can be produced on high-grade packaging or labels of a product that is or are intended to raise the value of the product.

With printing inks of the invention which comprise platelet-shaped, copper-containing, nonleafing effect pigments it is possible to produce a virtually perfect metal mirror in the case of what is called reverse application, where a transparent film is printed with the printing ink. This metal mirror becomes visible when the application is viewed from the film side, i.e., from the surface of the film facing away from the printed surface.

Printing inks of the invention which comprise platelet-shaped, copper-containing, leafing effect pigments can be used for surface printing on paper and cardboard, such as for cigarette packs, chocolate packs or labels, for example.

The solvent-based printing inks of the invention comprise metallic effect pigment preferably at a concentration between 3% and 35%, more preferably 5% to 30%, more preferably still 10% to 20%, by weight, at least one polymer-based binder preferably at a concentration of 1% to 40%, preferably of 1% to 30%, more preferably of 20 to 25%, even more preferably of 20 to 10%, by weight, solvent, based in each case on the total weight of the printing ink, and also of up to 15%, preferably of 0.1% to 9%, more preferably of 0.2% to 5%, even more preferably of 0.3% to 2.5%, by weight, of at least one further component, the FIGUREs in % by weight in relation to the at least one further component being based on the weight of copper-containing metallic effect pigment; and also, optionally, further auxiliaries.

The present invention also provides printing ink concentrates which in terms of their construction are similar to an organic solvent-based printing ink of the invention but possess a lower solvent fraction. In order to obtain a print-ready printing ink of the invention, solvent is added to the desired consistency or viscosity. Printing ink concentrates offer the advantage that, depending on the printing technology, the respective viscosity can be set by addition of solvent, and hence a printing ink concentrate can be used for different printing processes and printing machines.

The mixture according to the invention can be employed with particular preference in printing inks or printing ink concentrates for gravure, flexo, screen or digital printing.

The invention further provides a printing ink, preferably a gravure, flexographic, screen or digital printing ink, which comprises the mixture according to the invention, or a printing ink concentrate which comprises the mixture according to the invention.

This printing ink of the invention or this printing ink concentrate of the invention exhibits a significantly improved shelf life in comparison to printing inks or printing inks concentrates based on the specified platelet-shaped, copper-containing metallic effect pigments without the at least one further component according to the present invention. Thus, for example, a printing ink with the platelet-shaped, copper-containing metallic effect pigments specified in claim 1 without the at least one further component and polyvinyl butyral (PVB) as binder exhibits a significant increase in viscosity within the first few hours after production, and exhibits gelling within 24 hours.

The at least one further component, which is a cellulose derivative selected from the group consisting of alkylcellulose, hydroxyalkylcellulose, alkyl-(hydroxyalkyl)cellulose, and mixtures thereof, and/or is at least one additive having antioxidative and/or radical-inhibiting properties, is added to the mixture according to the invention or to the coating composition of the invention, in an amount of up to 15%, preferably from 0.1% to 9%, more preferably from 0.2% to 5%, even more preferably 0.3% and 2.5%, by weight, based in each case on the weight of copper-containing metallic effect pigment.

A combination of at least one additive having antioxidative and/or radical-inhibiting properties and a cellulose derivative selected from the group consisting of alkylcellulose, hydroxyalkylcellulose, alkyl(hydroxyalkyl)cellulose, and mixtures thereof, and preferably a corrosion inhibitor, is particularly preferred and exhibits significant stabilization of the coating composition of the invention, more particularly of printing inks.

The printing inks of the invention comprise—preferably organic—solvents or solvent mixtures. As well as dissolving the binders, these solvents/mixtures also serve to set important application properties of these printing inks, such as the viscosity or the drying rate, for example. Solvents used for gravure and flexo inks include, in particular, low-boiling solvents. The boiling point is generally not more than 140° C. Higher-boiling solvents are used only in smaller amounts, for the purpose of setting the drying rate.

Examples of particularly suitable solvents for liquid printing inks include ethanol, 1-propanol or 2-propanol, substituted alcohols, such as ethoxypropanol or methoxypropanol, or esters, such as ethyl acetate, isopropyl acetate, n-propyl acetate or n-butyl acetate, for example. It is of course also possible to use mixtures of different solvents. For example, a mixture of ethanol and esters such as ethyl acetate or n-propyl acetate may constitute such a mixture.

In a printing ink of the invention there is usually 10% to 80% by weight of solvent, based on the total weight of the printing ink. For printing with flexo inks it is preferred in accordance with the invention for the ester fraction of the total solvent not to exceed around 20% to 25% by weight.

For printing inks of the invention, a fraction of—preferably organic—solvent or a solvent mixture in the range from 60% to 80% by weight, based on the total weight of the printing ink, proves particularly advantageous.

Printing ink concentrates differ from printing inks in relation to the solvent fraction. The preferably organic solvent fraction in the printing ink concentrates of the invention is preferably in a range from 10% to 50%, more preferably from 12% to 30%, even more preferably from 15% to 25%, by weight, based in each case on the total weight of the printing ink concentrate. In order to obtain a ready-to-use printing ink, it is usual to add 40%-85% by weight of preferably organic solvent, based on the total weight of the printing ink concentrates.

As binders for the coating compositions of the invention, especially printing inks, it is possible in principle to use the binders that are customary for liquid printing inks, these binders being selected in accordance with the desired end application and the desired properties.

Examples of suitable binders include polyesters, polyamides, PVC copolymers, aliphatic and aromatic ketone resins, melamine-urea resins, melamine-formaldehyde resins, maleates, rosin derivatives, polyvinyl butyrals, casein and casein derivatives, ethylcellulose, and/or aromatic and aliphatic polyurethanes. Use may also be made of polymers and/or copolymers of vinyl acetate, vinyl alcohol, acrylates, methacrylates, vinylpyrrolidone and/or vinyl acetals.

Particular advantage attaches to using hyperbranched polymers containing functional groups, examples being hyperbranched polyurethanes, polyureas or polyester amides, as disclosed in WO 02/36695 and WO 02/36697. It is of course also possible to use mixtures of different polymeric binders. The amount of all the binders is usually 1% to 40%, preferably from 5% to 30%, more preferably from 8% to 25%, by weight, based on the total weight of the coating composition, preferably printing ink.

Particularly preferred binders include, for example, ethylcellulose, hydroxyethylcellulose, acrylates, polyvinyl butyrals, and also aliphatic and aromatic polyurethanes and polyureas, especially hyperbranched polyurethanes and polyureas, or mixtures thereof. Ethylcellulose is used preferably as a binder since it is particularly suitable for providing storage-stable, solvent-based printing inks of the invention on the basis of platelet-shaped, copper-containing effect pigments.

Ethylcellulose-based coating compositions, more particularly paints, printing inks or varnishes, which comprise additives having corrosion-inhibiting and/or antioxidative and/or radical-inhibiting properties exhibit an outstanding shelf life.

Ethylcellulose offers the advantage, moreover, that it can be used to formulate very brilliant printing inks, which are especially suitable for direct and reverse printing.

The mixture according to the invention and the coating compositions of the invention, preferably printing inks, paints, and varnishes, may further comprise one or more auxiliaries which are different from the at least one further component.

Examples of auxiliaries are fillers such as calcium carbonate, aluminum oxide hydrate, aluminum silicate and/or magnesium silicate. Waxes may enhance the abrasion resistance and serve to increase the lubricity. Examples are, in particular, polyethylene waxes, oxidized polyethylene waxes, petroleum waxes or ceresin waxes. Fatty acid amides may be used to increase the surface smoothness. Plasticizers serve to increase the elasticity of the dried film.

For dispersing the effect pigments in the mixture according to the invention or in the coating composition of the invention, dispersing assistants may be used.

Fatty acids may be used to bring about floating of the copper-containing metallic effect pigments in the printed layer, so that the pigments are accumulated at the upper boundary surface of the printed layer. Advantageously improved metallic effects may be achieved by this means. Furthermore, antisettling agents may also be added. Such additions prevent the sedimentation of the copper-containing metallic effect pigments. Examples include silica, cellulose derivatives, and waxes.

In formulating a particularly low-viscosity coating composition of the invention, such as a printing ink, as for example gravure inks or flexo inks, it is possible to add antisettling agents. The total amount of all the auxiliaries ought typically not to exceed 20% by weight, based on the total weight of the coating composition, preferably a printing ink, and is preferably in a range from 0.1% to 10% by weight, based on the total weight of the formulation.

A coating composition of the invention, such as a printing ink, for example, may be produced in a way which is known in principle, by intensely mixing and/or dispersing the constituents in typical apparatus, examples being dissolvers or stirring mechanisms. When dissolvers are used, care is taken to ensure that the energy input is not too high, so as to avoid damage to the copper-containing metallic effect pigments for use in accordance with the invention. The energy input is of course high enough to allow full dispersing of the pigments.

If further color pigments are used alongside the copper-containing metallic effect pigments for use in accordance with the invention, it may be advisable to predisperse these further pigments in a portion or in the entirety of the organic solvent, of the binder, and also, where appropriate, of further auxiliaries that are present, and only later to add the copper-containing metallic effect pigments for use in accordance with the invention.

In this way, any further color pigments used can be dispersed to particularly good effect, without causing damage by excessive dispersing to the copper-containing, metallic effect pigments for use in accordance with the invention.

In place of the copper-containing metallic effect pigments it is also possible to add predispersed copper-containing metallic effect pigment concentrates.

The present invention relates further to a coated article which comprises a mixture of copper-containing metallic effect pigments with at least one further component as described herein, or a coating composition as also described herein.

The article in question may be the body of an automobile, an architectural facing element, metal, printed product, paper, paperboard, cardboard, film/foil/sheet, glass, ceramic, stone, plastics, preferably polymeric moldings etc. More particularly the article may constitute labels, packaging, etc.

According to one preferred development of the invention, the article is transparent, preferably a transparent film. According to a preferred embodiment, the film is used in reverse application. These reverse applications on films are suitable, for example, for labels or packaging. In the case of a reverse application, the surface of the film faces toward the eye of an observer, i.e., the copper-containing metallic effect pigments are arranged on that surface of the film area that is facing away from the viewer. A reverse application offers the great advantage that the copper-containing metallic effect pigments are protected by the film from mechanical or chemical exposures, and generate an outstanding visual impression in respect of luster and color. In the case, for example, of labels for containers such as drinks bottles, perfume bottles, etc., the copper-containing metallic effect pigments, and the print, is not damaged when the containers strike one another. Moreover, the reverse application enables the provision of labels and packaging which are transparent except for the printed application of the copper-containing metallic effect pigments.

The invention further provides a method for producing a mixture of copper-containing metallic effect pigments with at least one further component as described herein, said method comprising the following steps:

(a) milling a copper-containing metal powder having a particle size distribution with a $d_{powder,50}$ of 1 to 180 µm and a $d_{powder,90}$ of 2 to 430 µm and having a copper content of 60% to 100% by weight, based on the total metal powder, to form platelet-shaped metallic effect pigments, using a milling mechanism, in the presence of lubricants and grinding media and optionally solvent, the resulting platelet-shaped metallic effect pigments having an average thickness, as determined via thickness counting by scanning electron microscopy (SEM), with an $h_{50}$ of 10 to 100 nm, preferably of 10 to 50 nm, and an $h_{90}$ of 20 to 150 nm, preferably of 20 to 70 nm, and (b) contacting the platelet-shaped metallic effect pigments obtained in step (a) with at least one further component which is a cellulose derivative selected from the group consisting of alkylcellulose, hydroxyalkylcellulose, alkyl (hydroxyalkyl)cellulose, and mixtures thereof, and/or is at least one additive having antioxidative and/or radical-inhibiting properties.

A starting material used in the milling step is copper-containing powder, such as copper powder or brass powder, for example.

In the case of copper powder, it is preferred to use high-purity copper obtained electrolytically. Where necessary, the copper powder is classified to give a copper powder having the necessary size distribution with a $d_{powder,50}$ of 1 to 180 μm, preferably of 1 to 15 μm, and a $d_{powder,90}$ of 2 to 430 μm, preferably of 2 to 27 μm.

The copper-containing powder used, brass powder for example, preferably has a size distribution with a $d_{powder,50}$ of 1 to 180 μm and a $d_{powder,90}$ of 2 to 430 μm. A powder of this kind is used preferably in the context of a dry milling.

Furthermore, a copper-containing powder, brass powder for example, is preferably used that has a size distribution with a $d_{powder,50}$ of 1 to 15 μm and a $d_{powder,90}$ of 2 to 27 μm. Such a powder is used preferably in the context of a wet milling.

Besides copper, the copper-containing metal powder may also comprise zinc and/or aluminum and also further metals. For example, brass may include 0.1% to 2% by weight of aluminum, based on the total metal content.

In the case of brass powder, it is preferred to use high-purity, electrolytically obtained copper and zinc and to alloy them preferably with addition of a little aluminum as reducing agent. For this purpose, copper and zinc are melted with one another and the brass melt produced is atomized to form a brass powder. The brass powder obtained in this way is preferably classified, using a cyclone, for example, in order to give a brass powder having the necessary size distribution with a $d_{powder,50}$ of 1 to 180 μm, preferably of 1 to 15 μm, and a $d_{powder,90}$ of 2 to 430 μm, preferably of 2 to 27 μm.

The copper-containing metal powder having the requisite size distribution, a copper or brass powder, for example, is subsequently milled to form platelet-shaped, copper-containing metallic effect pigments—copper or brass effect pigments, for example.

The milling of copper-containing metal powder, such as copper powder or brass powder, for example, takes place predominantly by the Hametag dry milling process. In this process, the copper-containing metal powder, copper or brass powder for example, is milled in ball mills in a number of milling stages under different milling conditions, such as mill size, mill diameter, rotational mill velocity, ball size, and milling time, for example, with addition of lubricant, such as stearic acid or oleic acid, for example, in order to prevent cold welding of the copper-containing metal particles, copper or brass particles for example, and with grinding media, such as steel balls, for example.

In the dry milling of copper-containing metal powder, as for example copper powder or brass powder, the copper-containing metal powder used, as for example copper powder or brass powder, is milled to give platelet-shaped, copper-containing metallic effect pigments. The density of the platelet-shaped, copper-containing metallic effect pigments, which are relatively difficult to deform, is around three times as high as that of comparable aluminum effect pigments. After milling and optional classifying have taken place, the platelet-shaped, copper-containing metallic effect pigments are collected in different containers and then homogenized and/or mixed. In order to give the subsequent, metallic effect-pigmented coatings the required metallic luster, it is possible, during subsequent aftertreatment, for additional auxiliaries (such as stearic acid, for example) to be "polished on" to the surface of the pigment platelets.

In the production of platelet-shaped, copper-containing metallic effect pigments having an $h_{50}$ of 10 to 50 nm and an $h_{90}$ of 20 to 70 nm, the copper-containing metal powder is subjected to wet milling.

For the wet milling of copper-containing metal powder, such as copper powder or brass powder, for example, said powder is milled in the presence of lubricant and solvent. Wet milling is preferred, being more gentle than dry milling.

In a further preferred embodiment, the copper-containing powder particles, as for example copper or brass particles, are milled in two stages.

In the first stage, the copper-containing powder particles, copper or brass particles for example, are subjected to primary deformation, and in the second stage they are milled until the completely flatly deformed platelet-shaped, copper-containing metallic effect pigments are obtained.

This primary deformation step is carried out preferably under conditions which allow a high energy input onto the copper-containing metal particles.

The two stages can be carried out, for example, with different sizes of grinding medium, e.g., ball sizes. In this case it is useful to select larger balls, allowing a higher energy input, in the primary deformation step. With this variant of the method, therefore, a two-stage operation is conducted, and this is more costly and inconvenient than a single-stage method.

In a further method variant, therefore, the two stages are carried out in one mill with the same grinding medium charge. In this case the difference in energy input can be brought about, for example, by different rotational speeds of the mill and/or by different milling times.

The copper-containing metal powder used for wet milling, a copper or brass powder, for example, is produced preferably in atomizers by atomization of a copper melt, a copper-containing melt, such as a brass melt, for example, such as a melt of a copper-zinc alloy, for example. The powder obtained following atomization of a copper, copper-containing or brass melt is classified according to one preferred variant, in order to give the desired particle size distribution, which may also be termed particle band.

The copper-containing metal powder, copper powder or brass powder for example, may, subsequent to the atomizing step, be brought to the desired narrow size distribution by means of corresponding classifying steps. Classifying can be carried out with air classifiers, cyclones, and other known installations. The use of a fine, copper-containing metal powder, copper powder or brass powder for example, with a narrow size distribution is of essential importance to the production of the platelet-shaped, copper-containing metallic effect pigments for use in accordance with the invention.

During the deformative milling, the copper-containing metal particles, copper or brass powder particles for example, are not deformed in a completely uniform way: This means that certain metal particles are deformed more greatly, while some of the powder particles are deformed only at a very late stage during milling. Among the reasons for this is the fact that the deformation probability for a metal particle is dependent on its size. Thus, metal particles which have already undergone primary deformation to platelets possess a higher specific surface area than metal powder which has not yet been deformed, and, accordingly, they possess a greater probability of being deformed further. The breadth of the size distribution of the metal powder is therefore reflected not only in the size distribution of the copper-containing metal platelets—copper or brass platelets, for example—formed from it, but also in the distribution of the thickness distribution. For narrow thickness distributions, therefore, it is necessary to use a copper or brass powder with a correspondingly low size variation.

The atomizing step can be carried out in an air atmosphere or under inert gas atmosphere. Inert gases used are preferably nitrogen and/or helium.

The purity of the copper or copper-zinc alloy (brass) used at the atomizing stage is preferably 99.0% to above 99.9% by weight. The powder may comprise, in correspondingly small amounts, the typical alloying constituents (e.g., Al, Si, Fe, Sn, Pb). It is preferred for 0.1%-2% by weight of aluminum to be alloyed in.

Wet milling of the copper-containing metal powder, as for example copper powder or brass powder, takes place in conventional mills, preferably in a ball mill, stirred ball mill, edge runner mill, drum ball mill or rotary tube ball mill, in the presence of solvent and lubricants as grinding assistants, and also using grinding media.

In the course of the wet milling, taking place in at least two steps, of the copper-containing metal powder, as for example copper powder or brass powder, use is made of grinding media, preferably spherical grinding media having an average diameter of 0.3 up to 4.7 mm and preferably of 0.6 to 2 mm.

The grinding media used in diverse embodiments, such as balls, ellipsoids, cylinders, cuboids, etc., for example, are composed preferably of chromium steel, steel, glass or ceramic. With particular preference the grinding media are composed of chromium steel. Furthermore, it is particularly preferred as grinding media to use preferably spherical media, more preferably balls.

Preferred spherical grinding media are those having a very smooth surface, a very round form, and uniform size.

The grinding media used for the wet milling of the copper-containing metal powder, as for example copper powder or brass powder, preferably have an individual weight of 85 µg to 425 mg.

According to one preferred development of the invention, the grinding media have an individual weight of 0.8 to 180 mg.

In the case of steel balls, the average individual weight is preferably in a range from 1 to 180 mg, preferably from 1.2 to 150 mg, more preferably from 2.0 to 120 mg. In the case of glass balls, the average individual weight is in a range from 1.0 to 12.5 mg.

On account of the extremely gentle mode of milling, the duration of this milling is comparatively long.

The milling time is preferably 10 to 100 hours, more preferably 20 to 60 hours, and very preferably 30 to 50 hours.

These times are understood to be the total milling times. If milling is carried out in two or more different steps, then the milling times of the individual steps must be added up accordingly.

These long milling times lead to a large number of pigment/grinding media impacts. As a result, the pigment is shaped very uniformly, producing a very smooth surface and a very narrow thickness distribution.

This cannot be achieved, generally, in a milling time of less than 10 hours. Milling times above 100 hours, in contrast, are more and more uneconomic.

The temperatures during the milling operation are in the range from 15° C. to 55° C. Temperatures in a range from 20° C. to 35° C. are preferred.

At the milling stage, copper-containing metal powder, such as copper-containing atomized metal powder, such as copper or brass (atomized) powder, of defined particle size is introduced together with solvent, such as white spirit for example, into a ball mill.

Solvents used may be commercially customary organic solvents, preferably white spirit, solvent naphtha, alcohols, glycols, esters, ethers, ketones or mixtures thereof.

Milling ought preferably to be carried out in solvents which are compatible with the subsequently planned application.

For application in a gravure ink, for example, solvents such as ethyl acetate, n-propyl acetate or isopropyl acetate are preferred.

The rewetting step which is typically practiced with aluminum pigments is not advisable here. In the case of rewetting, if it proves necessary, the metallic effect pigments, after milling, are largely freed from their solvent, under reduced pressure and at elevated temperatures, and are then pasted up again with the solvent that is compatible (and desired by the customer) for the particular end application.

Because of the very high specific surface areas of the metallic effect pigments for use in accordance with the invention, the rewetting step may be accompanied by unwanted instances of agglomeration of the metallic pigments. Milling ought therefore, preferably, to be carried out in solvents which are compatible with the subsequently planned application.

Milling is carried out preferably in a solvent with a weight ratio of solvent to metal particle of preferably 1.5:1 to 5:1 and more preferably of 2:1 to 4:1.

In order to prevent cold welding of the powder particles, addition is made of lubricant, such as oleic acid, stearic acid or else inhibitors, for example, in an amount which is dependent on the particular free specific surface area (BET) of the rolled-out copper-containing metallic effect pigments, as for example copper or brass effect pigments. Generally speaking, 1% to 30% by weight, and preferably 1.5% to 10% by weight, of lubricants are used, based on the weight of the copper-containing metal powder—copper or brass powder, for example.

Lubricants which can be used in the course of milling include a large number of compounds.

Mention may be made in particular here of the fatty acids that have been used for a long time, with alkyl radicals of 10 to 24 C atoms. It is preferred to use oleic acid or mixtures of different unsaturated fatty acids or mixtures of unsaturated and saturated fatty acids, leading to nonleafing pigments. In contrast to leafing pigments, which float to the surface in the application medium, nonleafing pigments undergo arrangement in an application medium, such as a paint or printing ink, for example. It is additionally possible to add long-chain amino compounds, for example, to the fatty acids. The fatty acids may be of animal or else of plant origin.

The lubricant should be added in not too small an amount, since otherwise, owing to the high degree of shaping of the copper-containing metal powder—copper powder or brass powder, for example—the very large surface areas of the platelet-shaped, copper-containing metallic effect pigments produced, copper or brass effect pigments for example, will be inadequately saturated by adsorbed lubricant. In that case, instances of cold welding occur. Typical amounts are therefore 1% to 30% by weight, preferably 2% to 15% by weight, of lubricant, based on the weight of the copper-containing metal powder used, such as copper or brass powder, for example.

A particularly preferred lubricant used is an additive, the additive comprising, as structural units, at least one carboxylic acid having at least four carbon atoms, and also at least one polyglycol ether, the carboxylic acid and the polyglycol ether being bonded covalently to one another.

In this case it is particularly preferred for the carboxylic acids or fatty acids to be at least partly esterified with a polyglycol ether.

Hence use may be made, for example, of the commercially available fatty acid polyglycol ester "P4100" from BYK-Chemie, Wesel, Germany, which is commercialized as a process auxiliary for plastics.

The weight ratio of grinding balls to metal particles is preferably 10:1 to 60:1, more preferably from 25:1 to 50:1.

In relation to milling in a ball mill, the critical speed $n_{crit}$ is an important parameter, indicating the point in time at which the balls are forced to the mill wall by the centrifugal forces, and milling virtually no longer takes place:

$$n_{crit} = \sqrt{\frac{g}{2\pi^2} \cdot \frac{1}{D}}$$

where D is the drum diameter and g is the gravitational constant.

The rotational speeds of the ball mill are preferably 20% to 95%, more preferably 50% to 90%, and very preferably 55% to 86% of the critical speed $n_{crit}$.

The rotational speeds must not be too high, so as to favor slow deformation of the metal particles. On the other hand, the copper-containing metal powder, especially brass or gold bronze powder—in contrast to atomized aluminum powder, for instance—requires a relatively high energy input and hence higher rotational speeds, owing to the lower ductility of brass or copper or copper-containing metal. In order to bring about slow deformation, lightweight grinding balls are also used with preference in the method of the invention.

In contrast to conventional milling processes, the copper powder, for example, copper-containing metal powder or brass powder in the method of the invention is predominantly not ground or comminuted, but instead is deformed very gently over a relatively long time period.

The conditions recited above result in a very gentle milling, where the metal powder is slowly shaped, and fractures of the metal particles as a result of ball impact with high kinetic energy are avoided.

The milled material is isolated by filtration, and the filter-cake obtained is milled in a further ball mill with spherical grinding media, solvent, and grinding additive.

The milled material is separated from the grinding balls by rinsing with solvent, and is subsequently concentrated.

In a further, preferred method step, the metallic effect pigments obtained may be subjected to size classification. This classification ought to be carried out gently, in order not to destroy the thin metallic pigments. The classifying operation may be, for example, a wet sieving, a decanting or else a separation by sedimentation (by means of gravity or by centrifuging). In the case of wet sieving, it is usually the coarse fraction that is sieved out. Subsequently, the suspension is separated from excess solvent (by means of a filter press, centrifuge or filter, for example).

The contacting of the copper-containing metallic effect pigments for use in accordance with the invention with the at least one further component may be accomplished by introducing the copper-containing metallic effect pigments into the at least one further component, such as a solution or dispersion comprising the at least one further component, for example. The at least one further component and also, optionally, binders may also be applied by spraying, in a fluidized bed, for example, to the copper-containing metallic effect pigments for use in accordance with the invention.

The at least one further component, which is a cellulose derivative selected from the group consisting of alkylcellulose, hydroxyalkylcellulose, alkyl-(hydroxyalkyl)cellulose, and mixtures thereof, and/or is at least one additive having antioxidative and/or radical-inhibiting properties, can also be introduced directly into a coating composition, such as a paint or printing ink, for example, and then the copper-containing metallic effect pigments can be added.

It is of course also possible for the copper-containing metallic effect pigments to be contacted in a first step with the at least one component first of all, and then introduced into a coating composition, such as a paint or printing ink, for example.

Also possible is the incorporation, first, of the copper-containing metallic effect pigments into a coating composition, such as a paint or printing ink, for example, provided the at least one further component is added likewise to the coating composition shortly after, preferably within 1 h, more preferably within 30 minutes, more preferably still within 15 minutes.

EXAMPLES

The examples given below illustrate the invention, but without restricting it.

For all of the inventive and comparative examples, copper-containing metallic effect pigments were used which took the form of a paste having an effect pigment content of 50% by weight. The copper-containing effect pigments were nonleafing effect pigments having a composition of 70% by weight copper and 30% by weight zinc. The solvent of the paste was methoxypropanol. The pigments had a diameter with a $d_{50}$ of 8 μm. The thickness distribution possessed an $h_{10}$ of 20 nm, $h_{50}$ of 25 nm, $h_{90}$ of 30 nm, and an $h_{98}$ of 32 nm.

Inventive Example 1

Preparation of a Copper-Containing Metallic Effect Pigment Paste with the Radical Inhibitor BHT (Butylated Hydroxyltoluene)

10 g of BHT (Sigma-Aldrich, St. Louis, USA) were dispersed in 90 g of methoxypropanol by means of a dispersing apparatus (Silverson L4RT; Silverson Machines Inc. UK). This solution was introduced and homogenized with 900 parts of the 50% by weight paste of copper-containing effect pigment in methoxypropanol, using the mixer Visco 5000 (Collomix, D-85080 Gaimersheim).

Inventive Example 2

Production of Granules Composed of Copper-Containing Effect Pigment, Additive, and a Synthetic Resin 15.0 g of Erkamar 3300 (Robert Kraemer GmbH & Co. KG, D-26180 Rastede) were dissolved in 50 g of isopropyl alcohol and homogenized by means of a dispersing apparatus (Silverson L4RT; Silverson Machines Inc. UK).

This solution was introduced into the mixture specified in example 1, and homogenized using a mixing apparatus. The paste amount used contained 85.0 g of copper-containing effect pigment. The homogenized preparation was processed into granules/sausages having a length of around 2-10 mm and a diameter of around 2-3 mm, using a press with ram and perforated plate (in-house construction, Eckart). Drying took place within 24 hours at 75° C. under reduced pressure (100 mbar) in a vacuum drying cabinet (VDL-23, Binder GmbH, D-78532 Tuttlingen).

Preparation of Solvent-Based Gravure Inks from Copper-Containing Effect Pigment, Polyvinyl Butyral, a Corrosion Inhibitor and/or an Antioxidant and/or Radical Inhibitor (Inventive Examples 3 to 8)

General Preparation:

For the preparation of the gravure inks, the solvents, in this case 30.4 parts of ethanol and 39 parts of ethyl acetate, were introduced, 0.5 part or 1.0 part of the respective additives was added, the mixture was stirred, and 3.5 parts of the binder, in this case a high-viscosity polyvinyl butyral Pioloform BS18 (Wacker, D-84489 Burghausen), were dissolved under moderate rotational speeds (3000-5000 rpm). This was done using a laboratory mixer of brand name Silverson L4RT (Silverson Machines Inc. UK). Thereafter the copper pigment-containing effect pigment paste was added, and dispersion took place with low-to-moderate speeds (3000 rpm).

For print application, the completed gravure inks were adjusted with a suitable solvent, in this case methoxypropanol, to a printing viscosity between of 25 sec in the DIN4 flow cup in accordance with DIN 53 211 (MTV Messtechnik, Cologne).

The gravure inks were then stored for a stability test for 10 weeks at 40° C. in a commercial drying cabinet (Heraeus Function Line T20, Heraeus Holding GmbH, D-63450 Hanau) and subjected at regular intervals to optical testing and viscosity testing. Storage at 40° C. for 10 weeks corresponds roughly to storage at room temperature for 6 months.

The gravure inks are prepared as described above.

Comparative Example 1

The gravure ink was prepared as described above in the section on "General preparation", but without additive, i.e., without antioxidant and without radical inhibitor.

Inventive Examples 3-8

3) Gravure ink contains the radical inhibitor BHT (butylated hydroxytoluene; Sigma-Aldrich, St. Louis, USA) used at 1% by weight.
4) Gravure ink contains the antioxidant α-tocopherol (Sigma-Aldrich, St. Louis, USA) used at 1% by weight.
5) Gravure ink contains 0.5% by weight of Irgacor L12 as corrosion inhibitor and 1% by weight of BHT as radical inhibitor.
6) Gravure ink contains 0.5% by weight of Irgacor L12 as corrosion inhibitor and 1% by weight of α-tocopherol as antioxidant.
7) Gravure ink contains 0.5% by weight of Irgamet 39 as corrosion inhibitor and 1% by weight of BHT as radical inhibitor.
8) Gravure ink contains 0.5% by weight of Irgamet 39 as corrosion inhibitor and 1% by weight of α-tocopherol as antioxidant.

Table 1 now describes the stability results for comparative example 1 and for inventive examples 3-8.

TABLE 1

Stability results of the individual printing inks after production and after storage at 40° C. for 10 weeks

| Examples | Viscosity after production in sec | Viscosity after storage for 10 weeks in sec |
| --- | --- | --- |
| Comp. ex. 1 | 25 | Not measurable, owing to excessive viscosity |
| Inv. ex. 3 | 25 | 102 |
| Inv. ex. 4 | 25 | 112 |
| Inv. ex. 5 | 25 | 56 |
| Inv. ex. 6 | 25 | 78 |
| Inv. ex. 7 | 25 | 67 |
| Inv. ex. 8 | 25 | 78 |

As described in table 1, all of the inventive printing inks exhibit a distinct increase in stability. The gravure ink without additives, used for purposes of comparison, gels completely after just a few hours, whereas the viscosity of the inventive printing inks rose slightly, but did not gel.

The first optical test was carried out by applying the printing ink to a suitable substrate, using a K Control Coater 632 applicator drawdown instrument (Testing Machines Inc., USA) and a laboratory model 628 Gravur-System Printing Proofer (Erichsen, D-58675 Hemer).

The printing inks were likewise proof-printed using the Rotova 300 printing machine (Rotocolor, Switzerland) on the film substrate PET (Melinex 400; Pütz GmbH+Co. Folien KG, D-65232 Taunusstein), and the pigmented film reverse applications were characterized optically by a gloss measurement at 60° in a method based on DIN 67 530 (instrument: micro-TRI-gloss from Byk-Gardner, D-82538 Geretsried). Calibration was carried out by means of dark calibration and also by means of a black mirror glass plate, with values of 92 for 60°.

The color density was measured using a densitometer (instrument: Densitometer, X-Rite, D-63263 Neu-Isenburg). Calibration took place with the aid of a white standard and with the aid of the unprinted substrate.

The definition of the color density of printed specimens is as follows:

Color density=−lg reflectance

The surfaces viewed are measured straight on.

The optical properties determined on the basis of printing machine proofs (printing machine: Rotova 300, printing method: gravure; printing speed 75 m/min, viscosity 15 s DIN-4 flow cup, 60, 70, 80, and 90 lines/cm) for the gravure inks from inventive examples 3-8 and comparative example 1 are set out in table 2 below.

The printing ink of comparative example 1 was prepared freshly for the printing test.

TABLE 2

Optical characterization of printing inks

| Examples | Gloss at 60° | | | | Color density | | | |
|---|---|---|---|---|---|---|---|---|
| | 60 l/cm | 70 l/cm | 80 l/cm | 90 l/cm | 60 l/cm | 70 l/cm | 80 l/cm | 90 l/cm |
| Comp. ex. 1 | 407 | 408 | 399 | 384 | 1.57 | 1.65 | 1.55 | 1.45 |
| Inv. ex. 3 | 410 | 409 | 399 | 384 | 1.56 | 1.62 | 1.52 | 1.44 |
| Inv. ex. 4 | 400 | 401 | 398 | 383 | 1.56 | 1.60 | 1.45 | 1.39 |
| Inv. ex. 5 | 390 | 391 | 386 | 370 | 1.50 | 1.50 | 1.40 | 1.30 |
| Inv. ex. 6 | 391 | 392 | 380 | 375 | 1.49 | 1.51 | 1.42 | 1.29 |
| Inv. ex. 7 | 388 | 389 | 380 | 370 | 1.48 | 1.47 | 1.38 | 1.38 |
| Inv. ex. 8 | 389 | 390 | 382 | 379 | 1.49 | 1.50 | 1.43 | 1.33 |

In table 2 it can clearly be seen that the additives present in the printing inks of the invention have little effect on the optical qualities of the printing inks. For the printing inks of the invention, the optical qualities are only slightly impaired as compared with the printing ink of comparative example 1. The desired mirror effect continues to be present with the printing inks of the invention.

When the printing inks described here are subjected to a stability test, it is no longer possible to print with the printing ink of comparative example 1, owing to gelling. In spite of the slight increase in viscosity, the printing inks of inventive examples 1 to 8 can be printed to give a good optical effect.

Preparation of a Solvent-Based Gravure Ink with Copper-Containing Effect Pigments, Ethylcellulose (Inventive Examples 9 and 10) or Nitrocellulose (Comparative Examples 2 and 3) and the Corrosion Inhibitor Irgacor L12 a) Printing Ink with Ethylcellulose Binder (Inventive Example 9):

A solvent-based gravure ink was prepared in accordance with the following formula. This was done using a laboratory mixer of the Silverson L4RT brand (Silverson Machines Inc. UK).

For the preparation of the printing ink, the solvent, in this case 25.4 parts of ethanol and 30 parts of ethyl acetate, was introduced, 0.6 part of the corrosion inhibitor Irgacor L12 was added, the mixture was stirred, and 4 parts of the binder, in this case the high-viscosity ethylcellulose Ethocel Std 200 (Dow, Midland, USA) were dissolved with moderate rotational speeds (3000-5000 rpm). Lastly, the paste (50% by weight of pigment in methoxypropanol with $d_{50}$=8 μm and $h_{50}$=25 nm) was added and was dispersed at low-to-moderate speeds (3000 rpm).

For print application, the completed printing ink was adjusted with a suitable solvent, in this case methoxypropanol, to a printing viscosity between of 25 sec in the DIN4 flow cup in accordance with DIN 53 211 (MTV Messtechnik, Cologne).

The printing ink was then stored for a stability test for 10 weeks at 40° C. in a commercial drying cabinet (see inventive example 3) and subjected at regular intervals to optical and viscosity testing. Storage at 40° C. for 10 weeks corresponds approximately to storage at room temperature for 6 months.

b) Printing Ink with Nitrocellulose Binder (Comparative Example 2):

A solvent-based gravure ink was prepared in accordance with the following formula. This was done using a laboratory mixer of the Silverson L4RT brand (Silverson Machines Inc. UK).

For the preparation of the printing ink, the solvent, in this case 30.4 parts of ethanol and 39 parts of ethyl acetate, was introduced, 0.6 part of the corrosion inhibitor Irgacor L12 and 1.0 part of the plasticizer acetyl tributyl citrate (Jungbunzlauer Ladenburg GmbH, D-68526 Ladenburg) was added, the mixture was stirred, and 2.3 parts of the binder, in this case the high-viscosity nitrocellulose E1160 (damping agent: isopropanol; Dow Wolff Cellulosics GmbH D-29656 Walsrode) were dissolved with moderate rotational speeds (3000-5000 rpm). Lastly, the paste (50% by weight of pigment in methoxypropanol with $d_{50}$=8 μm and $h_{50}$=25 nm) was added and was dispersed at low-to-moderate speeds (3000 rpm).

For print application, the completed printing ink was adjusted with a suitable solvent, in this case methoxypropanol, to a printing viscosity between of 25 sec in the DIN4 flow cup in accordance with DIN 53 211 (MTV Messtechnik, Cologne).

The printing ink was then stored for a stability test for 10 weeks at 40° C. in a commercial drying cabinet and subjected at regular intervals to optical and viscosity testing. Storage at 40° C. for 10 weeks corresponds approximately to storage at room temperature for 6 months.

Inventive Example 9

Printing ink (as described under a)) with ethylcellulose, without additives.

Comparative Example 2

Printing ink with nitrocellulose, without additives (as described under b)).

Inventive Example 10

Printing ink from comparative example 1, consists additionally of the corrosion inhibitor Irgacor 12 and the radical inhibitor BHT, used at 1.0% by weight (Ciba, D-68619 Lampertheim), used at 0.6% by weight.

Comparative Example 3

Printing ink from comparative example 2, additionally containing the corrosion inhibitor Irgacor 12 (Ciba, D-68619 Lampertheim) in an amount of 0.6% by weight.

Table 3 then sets out the stability results for the described examples 9 and 10 and also comparative examples 2 and 3.

TABLE 3

Stability results of the individual printing inks after production and after storage at 40° C. for 10 weeks

| Example | Viscosity after production in sec | Viscosity after storage for 10 weeks in sec |
|---|---|---|
| Inv. ex. 9 | 25 | 150 |
| Comp. ex. 2 | 25 | Not measurable, on account of excessive viscosity |
| Inv ex. 10 | 25 | 60 |
| Comp. ex. 3 | 25 | Not measurable, on account of excessive viscosity |

As can be seen in table 3, all of the printing inks of the invention based on the ethylcellulose binder exhibit a higher stability than the printing inks based on the nitrocellulose binder from the comparative examples. The printing ink from comparative example 2 gels completely after just a few hours, whereas for the ethylcellulose-based printing inks according to the invention there is no gelling, although the viscosity has risen.

The first optical test was carried out by applying the printing ink to a suitable substrate, using a K Control Coater 632 applicator drawdown instrument (Testing Machines Inc., USA) and a laboratory model 628 Gravur-System Printing Proofer (Erichsen, D-58675 Hemer).

The printing inks were likewise proof-printed using the Rotova 300 printing machine (Rotocolor, Switzerland), and the pigmented film reverse applications were characterized optically by a gloss measurement at 60° in a method based on DIN 67 530 (instrument: micro-TRI-gloss from Byk-Gardner, D-82538 Geretsried). Calibration was carried out by means of dark calibration and also by means of a black mirror glass plate, with values of 92 for 60°.

The color density was measured using a densitometer (instrument: Densitometer, X-Rite, D-63263 Neu-Isenburg). Calibration took place with the aid of a white standard and with the aid of the unprinted substrate.

The definition of the color density of printed specimens is as follows:
Color density=−lg reflectance
The surfaces viewed are measured straight on.

The optical properties determined on the basis of printing machine proofs (printing machine: Rotova 300, printing method: gravure; printing speed 75 m/min, viscosity 15 s DIN-4 flow cup, 60, 70, 80, and 90 lines/cm) are set out in table 4 below.

TABLE 4

Optical characterization of printing inks

| | Gloss at 60° | | | | Color density | | | |
|---|---|---|---|---|---|---|---|---|
| | 60 l/cm | 70 l/cm | 80 l/cm | 90 l/cm | 60 l/cm | 70 l/cm | 80 l/cm | 90 l/cm |
| Inv. ex. 9 | 466 | 464 | 444 | 430 | 1.46 | 1.45 | 1.43 | 1.38 |
| Comp. ex. 2 | 458 | 458 | 434 | 424 | 1.45 | 1.46 | 1.40 | 1.34 |
| Inv. ex. 10 | 442 | 440 | 410 | 400 | 1.44 | 1.42 | 1.36 | 1.28 |
| Comp. ex. 3 | 400 | 399 | 398 | 390 | 1.44 | 1.46 | 1.42 | 1.30 |

In table 4 it can clearly be seen that the optical qualities of the printing ink according to the invention, from inventive example 10, have only a slightly reduced gloss.

When these printing inks are then stored for a stability test, as described, the printing inks from comparative examples 2 and 3 can no longer be printed, owing to gelling. The printing inks from inventive examples 9 and 10 can be printed, despite the increase in viscosity, to give a good optical effect.

What is claimed is:

1. A mixture of platelet-shaped, copper-containing metallic effect pigments having a total metal content and having a copper content of 60% to 100% by weight, based on the total metal content, with at least one further component, wherein the copper-containing metallic effect pigments have a thickness distribution, determined via thickness counting by scanning electron microscopy (SEM) and represented as cumulative undersize distribution,
    a) with an $h_{50}$ of 10 to 100 nm,
    b) with an $h_{90}$ of 20 to 150 nm, and in that the at least one further component is at least one of a cellulose derivative selected from the group consisting of alkylcellulose, hydroxyalkylcellulose, alkyl(hydroxyalkyl)cellulose, and mixtures thereof, and at least one additive having at least one of antioxidative and radical-inhibiting properties.

2. The mixture as claimed in claim 1, wherein the copper-containing metallic effect pigments have a thickness distribution, determined via thickness counting by scanning electron microscopy (SEM) and represented as cumulative undersize distribution,
    a) with an $h_{50}$ of 10 to 50 nm, and
    b) with an $h_{90}$ of 20 to 70 nm.

3. The mixture as claimed in claim 1,
    wherein the additive is at least one of an antioxidant and a radical scavenger.

4. The mixture as claimed in claim 1,
    wherein in the mixture, in addition to the at least one further component, there is a corrosion inhibitor.

5. The mixture as claimed in claim 4,
    wherein the corrosion inhibitor is selected from the group consisting of fatty acids, carboxylic acid derivatives, organic phosphates and their esters and phosphonates and their esters, organically functionalized silanes, aliphatic or cyclic amines, aliphatic and aromatic nitro compounds, oxygen-, sulfur- or nitrogen-containing heterocycles, sulfur/nitrogen compounds of ketones, aldehydes and alcohols, thiols, beta-diketones, beta-keto esters, and mixtures thereof.

6. The mixture as claimed in claim 1,
wherein the additive having at least one of antioxidizing and radical-inhibiting properties is selected from the group consisting of phenols, phenol derivatives, quinones, quinone derivatives, nitroso compounds, nitrones, vitamin C, vitamin C derivatives, vitamin E, vitamin E derivatives, and mixtures thereof.

7. The mixture as claimed in claim 5,
wherein the carboxylic acid derivative is a partial ester of a dicarboxylic acid, tricarboxylic acid, tetracarboxylic acid or of a mixture thereof.

8. The mixture as claimed in claim 1,
wherein the mixture comprises an organic solvent or organic solvent mixture.

9. The mixture as claimed in claim 1, wherein the mixture is in compacted form.

10. The mixture as claimed in claim 9, wherein the compacted form is at least one selected from the group consisting of pellets, granules, tablets, briquettes and sausages.

11. A coating composition wherein the coating composition comprises a mixture as claimed in claim 1.

12. The coating composition as claimed in claim 11, wherein the coating composition is in compacted form.

13. The coating composition as claimed in claim 11, wherein the coating composition is at least one of a printing ink, a printing ink concentrate, a varnish, a varnish concentrate, a paint and a paint concentrate.

14. The coating composition as claimed in claim 12, wherein the compacted form is at least one selected from the group consisting of pellets, granules, tablets, briquettes and sausages.

15. A coated article
wherein the coated article comprises a mixture of copper-containing metallic effect pigments with at least one component as claimed in claim 1.

16. The coated article as claimed in claim 15, wherein the article is transparent.

17. The coated article as claimed in claim 16, wherein the transparent article is a transparent film.

18. A coated article wherein the coated article comprises a coating composition as claimed in claim 11.

19. The coated article as claimed in claim 18, wherein the article is transparent.

20. The coated article according to claim 19, wherein the transparent article is a transparent film.

21. A method for producing a mixture of copper-containing metallic effect pigments with at least one component as claimed in claim 1,
wherein the method comprises the following steps:
(a) milling a copper-containing metal powder having a particle size distribution with a $d_{powder,50}$ of 1 to 180 μm and a $d_{powder,90}$ of 2 to 430 μm and having a copper content of 60% to 100% by weight, based on the total metal powder, to form platelet-shaped metallic effect pigments, using a milling mechanism, in the presence of lubricants and grinding media and optionally solvent, the resulting platelet-shaped metallic effect pigments having an average thickness, as determined via thickness counting by scanning electron microscopy (SEM), with an $h_{50}$ of 10 to 100 nm and an $h_{90}$ of 20 to 150 nm, and
(b) contacting the platelet-shaped metallic effect pigments obtained in step (a) with at least one component, wherein said component is at least one of a cellulose derivative selected from the group consisting of alkylcellulose, hydroxyalkylcellulose, alkyl(hydroxyalkyl)cellulose, and mixtures thereof, and at least one additive having at least one of antioxidative and radical-inhibiting properties.

* * * * *